(12) United States Patent
Selvitelli et al.

(10) Patent No.: US 8,696,704 B2
(45) Date of Patent: Apr. 15, 2014

(54) METHODS AND DEVICES FOR REPAIRING TISSUE

(75) Inventors: David M. Selvitelli, Millis, MA (US);
Thomas C. May, Wrentham, MA (US);
Debra Mack, Walpole, MA (US);
Stuart E. Fromm, Rapid City, SD (US);
Christopher A. Battles, Hamden, CT (US)

(73) Assignee: DePuy Mitek, LLC, Raynham, MA (US)

( * ) Notice: Subject to any disclaimer, the term of this patent is extended or adjusted under 35 U.S.C. 154(b) by 1113 days.

(21) Appl. No.: 12/025,334

(22) Filed: Feb. 4, 2008

(65) Prior Publication Data

US 2008/0188893 A1 Aug. 7, 2008

Related U.S. Application Data

(63) Continuation of application No. 10/708,308, filed on Feb. 24, 2004, now Pat. No. 7,390,332.

(51) Int. Cl.
*A61B 17/04* (2006.01)

(52) U.S. Cl.
USPC ........................................................ 606/232

(58) Field of Classification Search
USPC ........... 606/232, 74, 213, 224, 228, 142, 143, 606/151; 623/13.11–13.16; 600/37
See application file for complete search history.

(56) References Cited

U.S. PATENT DOCUMENTS

| | | | |
|---|---|---|---|
| 2,738,790 A | 3/1956 | Todt, Sr. et al. | |
| 4,961,741 A | 10/1990 | Hayhurst | |
| 5,085,661 A | 2/1992 | Moss | |
| 5,470,337 A | 11/1995 | Moss | |
| 5,507,704 A | 4/1996 | Lasoen et al. | |
| 5,569,306 A | 10/1996 | Thal | |
| 5,728,136 A | 3/1998 | Thal | |
| 5,810,848 A | 9/1998 | Hayhurst | |
| 5,891,168 A | 4/1999 | Thal | |
| 6,066,146 A | 5/2000 | Carroll et al. | |

(Continued)

FOREIGN PATENT DOCUMENTS

| | | |
|---|---|---|
| JP | 2002058676 | 2/2002 |
| WO | 01/39671 | 6/2001 |
| WO | 02/36020 | 5/2002 |

OTHER PUBLICATIONS

AU Office Action dated Nov. 3, 2005 for AU Appl. No. 2005200304.

(Continued)

*Primary Examiner* — Corrine M McDermott
*Assistant Examiner* — Christopher L Templeton (57) ABSTRACT

Suture anchor systems for repairing torn or damaged tissue are described herein. In one embodiment, a system can include a first suture loop having a first suture anchor coupled thereto, the first suture loop including a slip knot formed thereon to allow a size of the first suture loop to be adjusted. The system can also include a second suture loop coupled to the first suture loop and having a second suture anchor coupled thereto. The second suture loop can have a fixed size. In use, the suture anchors can be deployed through tissue to be repaired and into the anchoring tissue at a position spaced apart from one another by a selected distance. The length of the first suture loop can then be tensioned to re-approximate the torn or damaged tissue toward the anchoring tissue, thereby securely attached the torn tissue to the anchoring tissue.

7 Claims, 8 Drawing Sheets

(56) References Cited

U.S. PATENT DOCUMENTS

| | | |
|---|---|---|
| 6,143,017 A | 11/2000 | Thal |
| 6,500,184 B1 * | 12/2002 | Chan et al. .................... 606/144 |
| 7,004,970 B2 * | 2/2006 | Cauthen, III et al. ...... 623/17.16 |
| 7,153,312 B1 * | 12/2006 | Torrie et al. .................... 606/144 |
| 7,390,332 B2 | 6/2008 | Selvitelli et al. |
| 2001/0041916 A1 | 11/2001 | Bonutti |
| 2001/0049537 A1 | 12/2001 | Kortenbach |
| 2002/0019649 A1 | 2/2002 | Sikora et al. |
| 2002/0173800 A1 | 11/2002 | Dreyfuss et al. |
| 2002/0198542 A1 | 12/2002 | Yamamoto et al. |
| 2003/0130694 A1 * | 7/2003 | Bojarski et al. .............. 606/228 |
| 2003/0229296 A1 | 12/2003 | Ishikawa et al. |
| 2004/0002734 A1 * | 1/2004 | Fallin et al. ................... 606/232 |
| 2004/0138683 A1 * | 7/2004 | Shelton et al. ................ 606/151 |
| 2004/0147958 A1 * | 7/2004 | Lam et al. ..................... 606/232 |
| 2004/0153074 A1 | 8/2004 | Bojarski et al. |
| 2005/0107828 A1 * | 5/2005 | Reese ........................... 606/232 |
| 2005/0251208 A1 * | 11/2005 | Elmer et al. ................... 606/232 |
| 2006/0142784 A1 * | 6/2006 | Kontos .......................... 606/139 |

OTHER PUBLICATIONS

CA Office Action dated Dec. 15, 2006 for CA Appl. No. 2,498,206.
EP Office Action dated Mar. 28, 2006 for EP Appl. No. 05251059.
EP Search Report dated Jun. 20, 2005 for EP Appl. No. 05251059.
JP Office Action dated Aug. 17, 2010 for JP Appl. No. 2005-047599.
JP Office Action dated Nov. 30, 2010 for JP Appl. No. 2005-047599.

* cited by examiner

METHODS AND DEVICES FOR REPAIRING TISSUE

CROSS-REFERENCE TO RELATED APPLICATION

The present application is a continuation of U.S. application Ser. No. 10/708,308 now U.S. Pat. No. 7,390,332, filed on Feb. 24, 2004 and entitled "Methods and Devices for Repairing Tissue," which is hereby incorporated by reference in its entirety.

FIELD OF THE INVENTION

The present invention relates to methods and devices for repairing torn or damaged tissue, and in particular to methods and devices for anchoring torn or damaged tissue using adjustable suture lengths.

BACKGROUND OF THE INVENTION

A variety of injuries and conditions require repair of soft tissue, or reattachment of soft tissue to bone and/or surrounding tissue. For example, when otherwise healthy tissue has been torn away from a bone, surgery is often required to reattach the tissue to the bone to allow healing and a natural reattachment to occur. A number of devices and methods have been developed to re-attach soft tissue to bone, and some of the more successful methods involve the use of suture anchors, which typically include an anchor body having a suture attachment feature, and a bone or tissue engaging feature for retaining the suture anchor within bone and/or tissue. Surgery can also be required when a tear occurs in the tissue, for example in the menisci. The simplest method of repairing such a tear is to stitch it closed by passing a length of suture through the tissue and tying the suture. The length of suture can also be used in conjunction with a suture anchor.

While many suture anchors devices for re-attaching soft tissue to bone and/or repairing torn tissue have been successful, they are not without their drawbacks. Many suture anchors, for example, require one or more knots to be formed to secure the suture to the bone and/or tissue. The knotting process can be difficult and tedious, particularly during laparoscopic or endoscopic procedures, where the surgeon must remotely manipulate the suture using tools inserted through an endoscopic tube. Further, several knots are often required to secure one suture. The knots may also "stand proud" above the tissue and interfere with movement and healing.

Other suture anchors utilize a knotless system that allows the suture to be tensioned to secure the suture to bone and/or tissue. Knotless suture anchors typically include a suture that is attached to an anchor, and a loop for receiving the free ends of the suture. While these structures can be secured without knots, the anchor used to secure the suture may itself stand proud above the tissue, causing discomfort and interfering with healing. Recently, knotless anchors have been developed that allow multiple anchors to be deployed using a single length of suture. While these systems eliminate the need to secure each suture anchor individually, they do not allow the tension of the suture to be adjusted individually with respect to each suture anchor.

Accordingly, there remains a need for improved methods and devices for repairing torn or damage tissue, and in particular for methods and devices for repairing torn and/or damaged tissue using multiple suture lengths. There also remains a need for methods and devices that reduce the risk of damage to the tissue being repaired, and that provide a low profile to eliminate interference with movement and healing.

SUMMARY OF THE INVENTION

The present invention provides a suture anchor system for repairing torn or damaged tissue. In general, the suture anchor system includes a first suture anchor having at least one length of suture attached thereto, and a second suture anchor having at least one length of suture attached thereto. Each length of suture is coupled to one another such that a distance between the first and second suture anchors with respect to each other can be selectively adjusted.

In one embodiment, first and second suture lengths can be slidably connected to one another by a third suture length extending therebetween. For example, each of the first, second, and third suture lengths can include a suture loop formed thereon, and the suture loop on the third suture length can be connected to the suture loop on each of the first and second suture lengths. The first and second suture anchors are preferably attached to the first and second suture lengths, respectively. At least one of the suture loops can also optionally include a slip knot that enables adjustment of a size of the suture loop. In an exemplary embodiment, the slip knot is formed on each of the first and second suture lengths, and the third suture length has a suture loop with opposed terminal ends that are fixedly mated to one another. Alternatively, the suture loop on each of the first and second suture lengths can be formed from opposed terminal ends of the suture length being fixedly connected to one another, and the suture loop on the third suture length can include a slip knot formed thereon that enables adjustment of a size of the suture loop.

In yet another embodiment, the first and second suture lengths can be connected to one another by a slip knot formed on one of the first and second suture lengths. By way of non-limiting example, the first and second suture lengths can each include first and second opposed terminal ends. The first terminal end of the first suture length can be connected to the first suture anchor, and second, opposed terminal end can remain as a free, trailing end. The first terminal end on the second suture length can be connected to a portion of the first suture length by a slip knot that allows the first terminal end of the second suture length to slidably move along the first suture length, and the second terminal end on the second suture length can be connected to the second suture anchor.

In other aspects of the present invention, the first suture length can include a suture loop formed thereon and coupled to a suture loop formed on the second suture length. Each suture loop preferably contains the suture anchor. The suture loop on each of the first and second suture lengths can also include a slip knot formed thereon to allow a size of each suture loop to be adjusted. Alternatively, only one of the suture loops, e.g., the suture loop on the first suture length, can include a slip knot formed thereon to allow a size of the suture loop to be adjusted, and the other suture loop, e.g., the suture loop on the second suture length, can have a fixed size. The fixed length can be formed from opposed terminal ends of the suture length being fixedly attached to one another.

The present invention also provides a method for anchoring tissue that includes the steps of inserting a first anchor member having a first suture length attached thereto through tissue to be repaired and into an anchoring tissue, and inserting a second anchor member having a second suture length attached thereto through the tissue to be repaired and into the anchoring tissue at a position spaced apart from the first anchor member by a selected distance. The second suture length on the second anchor member is preferably adjustably coupled to the first suture length on the first anchor member. The method further includes the step of tensioning at least one of the first and second suture lengths to anchor the tissue to be repaired to the anchoring tissue. At least one of the first and second suture lengths can be tensioned by pulling on a terminal end of the suture. In an exemplary embodiment, the tissue being repaired is the meniscus of the knee.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a suture anchor system for repairing torn or damaged tissue. In general, the suture anchor system includes a first suture anchor having at least one length of suture attached thereto, and a second suture anchor having at least one length of suture attached thereto. Each length of suture is coupled to one another such that a distance between the first and second suture anchors with respect to each other can be selectively adjustable. The suture anchor system also preferably includes at least one slip knot that allows the first and second suture anchors to be maintained in a fixed position with respect to one another. In use, the suture anchors can be deployed through tissue to be repaired, at a position spaced apart from one another by a selected distance, and into an anchoring tissue. The suture length(s) can then be tensioned to re-approximate the torn or damaged tissue toward the anchoring tissue, thereby securely attaching the torn tissue to the anchoring tissue.

While the suture anchor systems of the present invention can have a variety of configurations, FIGS. 1-5 illustrate various exemplary suture anchor systems, each of which has first and second suture lengths that are coupled to one another such that a distance between the first and second suture anchors with respect to each other can be selectively adjustable. A person skilled in the art will appreciate that the term "suture length" generally refers to a length of suture that includes first and second terminal ends. Moreover, while virtually any type of suture material can be used, each suture length is preferably formed from a non-absorbable material, such as Ethibond®, manufactured by Ethicon, Inc., a Johnson & Johnson company, or an absorbable material, such as Panacryl®, also manufactured by Ethicon, Inc., a Johnson & Johnson company.

Figure 1:
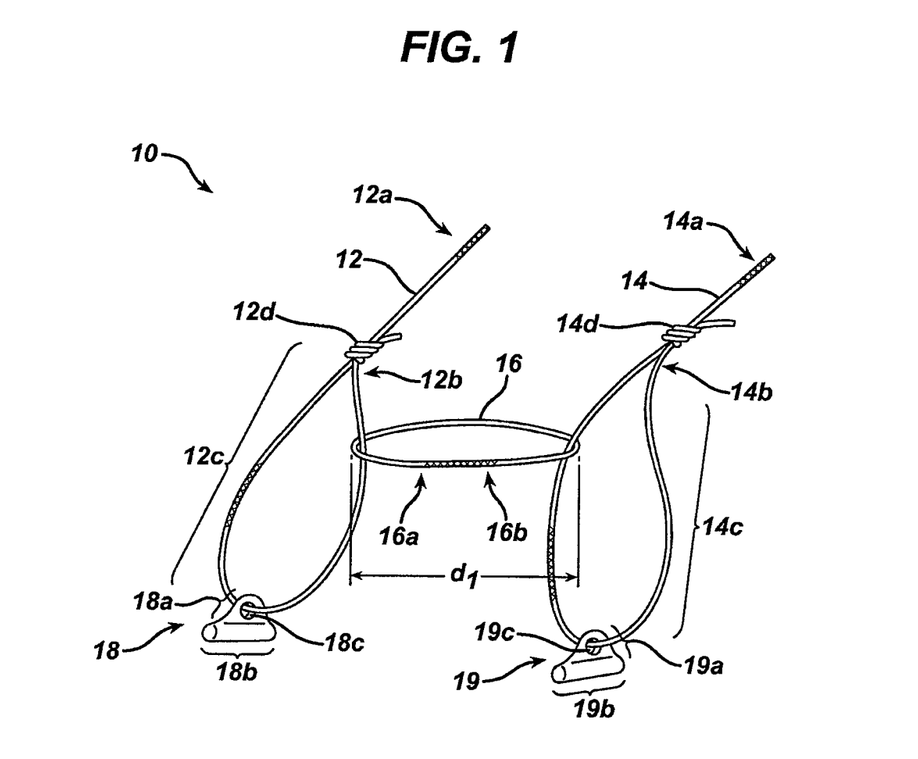
FIG. 1 is perspective view of one embodiment of a suture anchor system having a first suture length with an adjustable suture loop formed thereon containing a first suture anchor, a second suture length with an adjustable suture loop formed thereon containing a second suture anchor, and a third suture length in the form of a suture loop coupled to the suture loop on each of the first and second suture lengths.

FIG. 1 illustrates a suture anchor system 10 that includes first and second suture lengths 12, 14 that are coupled to one another by a third suture length 16. The first and second suture lengths 12, 14 each include a first terminal end 12a, 14a, and a second terminal end 12b, 14b. The first terminal end 12a, 14a of each suture length 12, 14 serves as the free end which can be used to tension the suture length 12, 14, as will be discussed in more detail below, and the second terminal end 12b, 14b is attached to a portion of the suture length 12, 14 to form a suture loop 12c, 14c. While a variety of techniques can be used to attach the second terminal ends 12b, 14b to the suture lengths 12, 14, a knot 12d, 14d that is slidably movable along the suture length 12, 14 is preferably used. In an exemplary embodiment, the knot 12d, 14d is a conventional slip knot 12d, 14d, such as a hangman knot or a fisherman knot. A slip knot 12d, 14d allows a size of the suture loop 12c, 14c to be adjusted, and it is also effective to lock the suture anchors 18, 19 in a fixed position with respect to one another, as will also be discussed in more detail below. Regardless of the technique used to mate the second terminal end 12b, 14b to the suture length 12, 14, the first terminal end 12a, 14a should extend from the knot 12d, 14d to form a free, trailing end of the suture length 12, 14 that can be used to tension the suture length 12, 14, thereby decreasing the size of the suture loop 12c, 14c.

The first and second suture lengths 12c, 14c also include a suture anchor 18, 19 mated to or disposed on the suture loop 12c, 14c portion of each suture length 12c, 14c. In an exemplary embodiment, each suture anchor 18, 19 is slidably disposed on the suture loop 12c, 14c of each suture length 12, 14 to allow the anchors 18, 19 to slide as the size of the loop 12c, 14c is adjusted. The configuration of the suture anchors 18, 19 can vary, and a person skilled in the art will appreciate that virtually any type of anchor device can be used with the present invention. In the illustrated embodiment, however, each anchor 18, 19 includes a suture-receiving portion 18a, 19a having a bore 18c, 19c formed therein for slidably receive the suture length 12, 14, and a tissue-engaging portion 18b, 19b that is adapted to engage tissue.

As stated above, suture anchor system 10 also includes a third suture length 16 that is coupled to each of the first and second suture lengths 12, 14. While various techniques can be used to couple the third suture length 16 to the first and second sutures length 12, 14, FIG. 1 illustrates a third suture length 16 that is in the form of a suture loop which extends between and is coupled to each of the first and second sutures loops 12c, 14c on the first and second suture lengths 12, 14. The third suture length, hereinafter referred to as suture loop 16, can be formed by mating terminal ends of the suture length 16a, 16b to one another. This can be achieved by, for example, tying the ends 16a, 16b to one another, ultrasonically bonding the ends 16a, 16b to one another, or using other techniques known in the art. In use, the third suture loop 16 serves as a bridge that extends between the first and second suture lengths 12, 14, and that extends across the tissue surface of the tissue being repaired. Accordingly, the size of the third suture loop 16 can be adapted depending on the particular procedure being performed. In an exemplary embodiment, however, the third suture loop 16 preferably has a diameter $d_1$ that substantially corresponds to an intended distance between the first and second suture anchors 18, 19 when the suture anchors 18, 19 are deployed through the tissue to be repaired and into the anchoring tissue.

Figure 2:
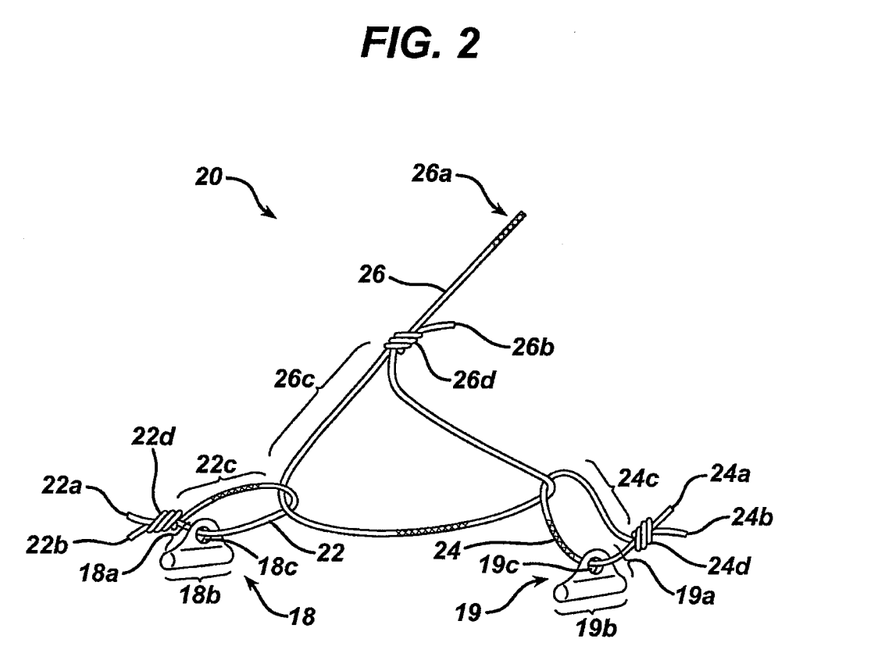
FIG. 2 is a perspective view of another embodiment of a suture anchor system having a first suture length with a fixed-length suture loop formed thereon containing a first suture anchor, a second suture length with a fixed-length suture loop formed thereon containing a second suture anchor, and a third suture length having an adjustable suture loop that is coupled to the suture loops on each of the first and second suture lengths.

In another embodiment, as shown in FIG. 1, the third suture loop 16 can optionally be adjustable, as shown in FIG. 2. In this embodiment, the suture anchor system 20 includes first and second suture lengths 22, 24 having fixed-length suture-loops 22c, 24c, and a third suture length 26 having an adjustable suture loop 26c that extends between and that is coupled to the first and second suture loops 22c, 24c. The fixed length on the first and second suture loops 22, 24 can be formed by fixedly mating the first and second terminal ends 22a, 22b, 24a, 24b to one another to form a suture loop 22c, 24c having a suture anchor 18, 19 slidably disposed thereon. In an exemplary embodiment (not shown), the terminal ends 22a, 22b, 24a, 24b are mated to one another, e.g., by forming a knot 22d, 24d, and each suture loop 22c, 24c is then passed through the bore 18c, 19c formed in the suture anchor 18, 19, such that the knot 22d, 24d retains the suture anchor 18, 19 thereon. As previously stated, a variety of other techniques can be used to fixedly mate the terminals ends 22a, 22b, 24a, 24b to one another.

The third suture length 26 is similar to the first and second suture lengths 12 and 14 described in connection with FIG. 1, and it includes a first terminal end 26a that serves as the free end which can be used to tension the suture length 26, as will be discussed in more detail below, and a second terminal end 26b that is attached to a portion of the suture length 26 to form a suture loop 26c. The suture loop 26c extends between and is coupled to the first and second suture loops 22c, 24c on the first and second suture lengths 22, 24. As was also described above with respect to FIG. 1, the second terminal end 26b of the suture length 26 is preferably attached to a portion of the suture length 26 using a slip knot 26d, as shown, or any other type of knot that allows slidable movement of the second terminal end 26b along the suture length 26.

In use, the third suture length 26 serves as a bridge that extends between the first and second suture lengths 22, 24, and that extends across the tissue surface of the tissue being repaired. Once the first and second suture anchors 18, 19 are deployed through the tissue to be repaired and into the anchoring tissue, the terminal, free end 26a of the third suture length 26 can be tensioned to decrease the size of the suture loop 26c and pull the suture taught between the first and second suture lengths 22, 24, thereby re-approximating and securing the torn or damaged tissue to the anchoring tissue.

Figure 3:
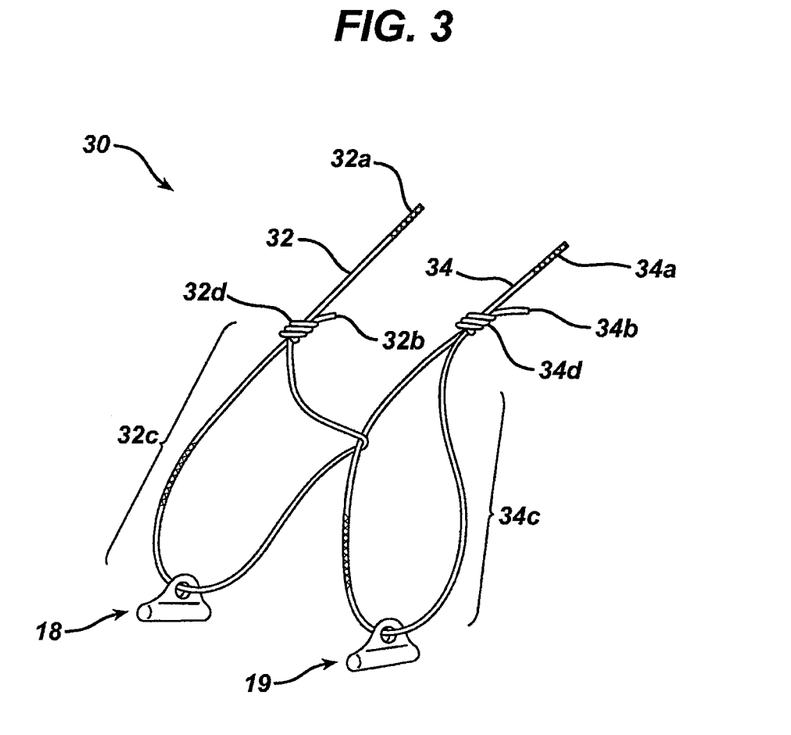
FIG. 3 is a perspective view of a suture anchor system in accordance with another embodiment of the present invention having a first suture length with an adjustable suture loop formed thereon containing a first suture anchor, a second suture length with an adjustable suture loop formed thereon containing a second suture anchor, and coupled to the suture loop on the first suture length.

In yet another embodiment of the present invention, the first and second suture lengths can be coupled directly to one another, rather than being coupled to one another by a third suture length. FIG. 3 illustrates one technique for coupling the first and second suture lengths to one another without using a third suture length. As shown, the suture anchor system 30 generally includes a first suture length 32 having a first terminal end 32a that serves as a free end, and a second terminal end 32b that is attached to a portion of the suture length 32, preferably using a sliding knot 32d, to form a suture loop 32c. The suture anchor system 30 also includes a second suture length 34 having a first terminal end 34a that serves as a free end, and a second terminal end 34b that is attached to a portion of the suture length 34, preferably using a sliding knot 34d, to form a suture loop 34c. The first and second suture loops 32c, 34c are each coupled to one another, as shown, and each loop 32c, 34c includes a tissue anchor 18, 19 slidably disposed thereon. In use, the first and second suture anchors 18, 19 are deployed through tissue to be repaired and into anchoring tissue, and the suture loops 32c, 34c serve as a bridge that extends between the first and second suture anchors 18, 19, and that extends across the tissue surface of the tissue being repaired. The free terminals end 32a, 34a of each suture length 32, 34 can be tensioned to decrease the size of each suture loop 32c, 34c to pull the suture loops 32c, 34c taught with respect to one another, thereby re-approximating and securing the torn or damaged tissue to the anchoring tissue.

Figure 4:
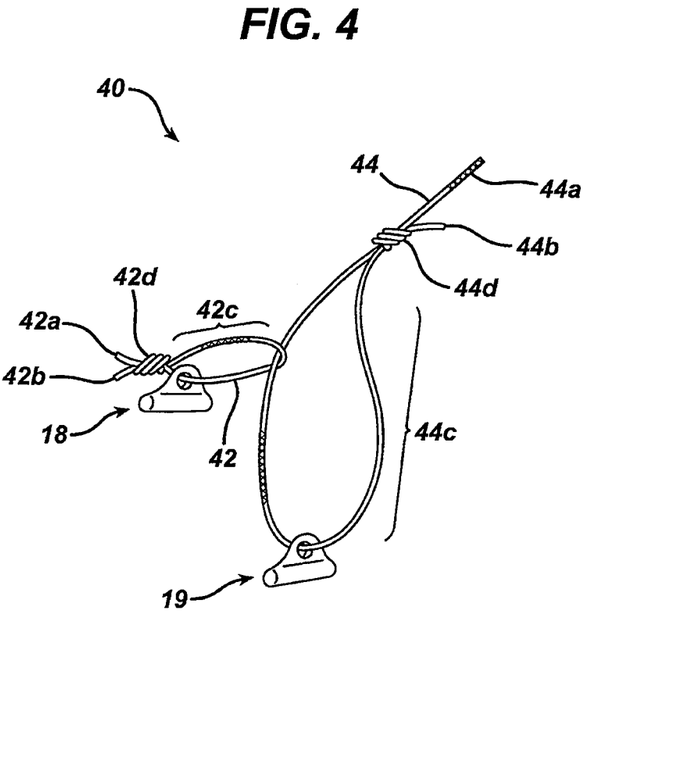
FIG. 4 is a perspective view of yet another embodiment of a suture anchor system having a first suture length with a fixed-length suture loop formed thereon and containing a first suture anchor, and a second suture length with an adjustable suture loop formed thereon containing a second suture anchor, and coupled to the suture loop on the first suture length.

FIG. 4 illustrates yet another embodiment of a suture anchor system 40 having first and second suture lengths 42, 44 that are directly coupled to one another. In this embodiment, one of the suture lengths, e.g., suture length 42, has a fixed diameter, and the other suture length, e.g., suture length 44, is adjustable. In particular, suture length 42 includes terminal ends 42a, 42b that are fixedly mated to one another, i.e., by tying the terminals ends 42a, 42b to one another to form a knot 42d, thereby forming a suture loop 42c. A suture anchor 18 is slidably disposed on the suture loop 42c. The second suture length 44 includes a first terminal end 44a, that serves as a free end, and a second terminal end 44b that is attached to a portion of the suture length 44, preferably using a sliding knot 44d, to form a suture loop 44c. In use, the suture loop 42c of the second suture length 42 serves as a bridge that extends between the first and second suture anchors 18, 19, and that extends across the tissue surface of the tissue being repaired. Depending on the diameter of the first suture loop 42c, a portion of the first suture loop 42c can also serve as a bridge that extends across at least a portion of the tissue surface. The free terminal end 44a of the second suture length 44 can be tensioned to decrease the size of the suture loop 44c, thereby re-approximating and securing the torn or damaged tissue to the anchoring tissue.

Figure 5:
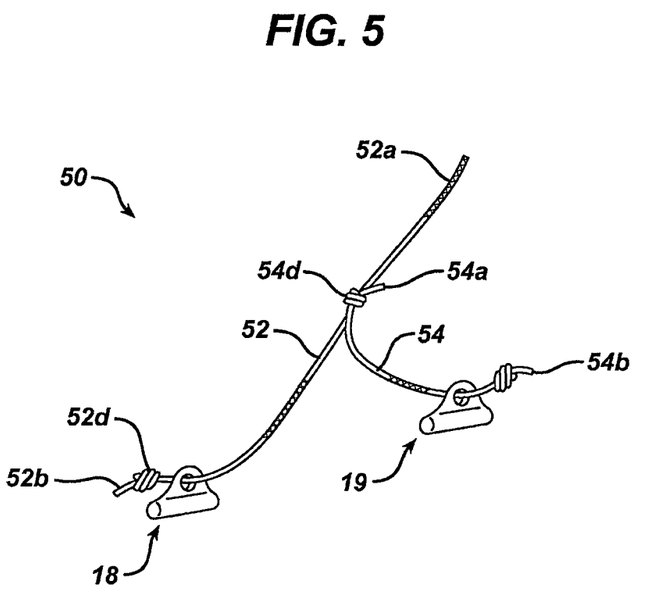
FIG. 5 is a perspective view of a suture anchor system having a first suture length with a first terminal end coupled to a first suture anchor, and a second, terminal end that serves as a free end, and a second suture length having a first terminal end coupled to a second suture anchor and a second terminal end that is slidably coupled to the first suture length, in accordance with yet another embodiment of the present invention.

FIG. 5 illustrates yet another embodiment of a suture anchor system 50 in accordance with the present invention. As shown, the suture anchor system 50 includes first and second suture lengths 52, 54, each having a first terminal end 52a, 54a, and a second terminal end 52b, 54b that is mated to a suture anchor 18, 19. The first terminal end of the one of the suture lengths, e.g., terminal end 52a of the first suture length 52, forms a free trailing end, and the first terminal end of the other suture length, e.g., terminal end 54a of the second suture length 52, slidably mated to a portion of the first suture length 52, preferably by forming a slip knot with the second terminal end 54a of the second suture length 54. This allows the first terminal end 52a of the first suture length 52 to serve as a free end that can be used to adjust the length of suture that extends between the first and second suture anchors 18, 19. In particular, when the first and second anchors 18, 19 are deployed through tissue to be repaired and into anchoring tissue, the first terminal end 52a of the first suture length 52 can be tensioned to re-approximate and secure the torn or damaged tissue to the anchoring tissue.

As stated above, the second terminal end 52b, 54b of each suture length 52, 54 is mated to a suture anchor 18, 19, and virtually any mating technique known in the art can be used. For example, the suture anchor 18, 19 can be fixedly attached to the terminal end 52a, 54a, or it can be slidably disposed on the suture length 52, 54, as shown in FIG. 5. This is achieved by forming a knot 52d, 54d at the end of the suture length 52, 54, and positioning the suture anchor 18, 19 along the suture length 52, 54 between the knot 52d, 54d and the first terminal end 52a, 54a.

A person skilled in the art will appreciate that the suture anchor systems of the present invention can have a variety of other configurations, and that a variety of other techniques can be used to allow a suture length(s) extending between two suture anchors to be adjusted to re-approximate torn or damaged tissue and attached the tissue to an anchoring tissue. Moreover, while the suture anchor systems are described as having only two suture anchors 18, 19, the suture anchor systems can be used with any number of anchor devices.

Figure 6A:
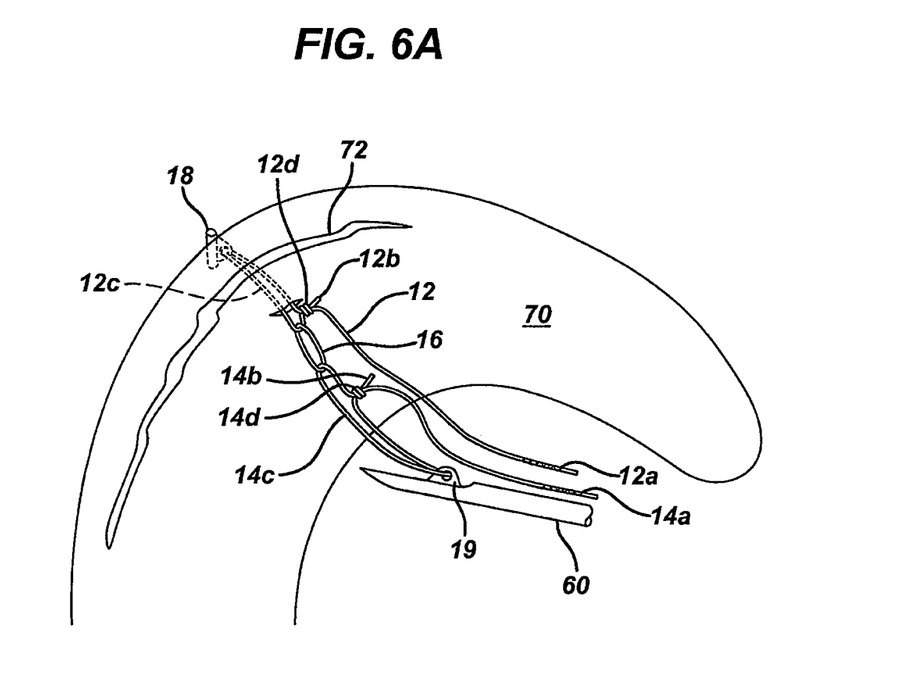
FIG. 6A is a perspective view illustration of a method for implanting a suture anchor system in accordance with the present invention, showing a first suture anchor implanted through tissue to be repaired and into an anchoring tissue.
Figure 6B:
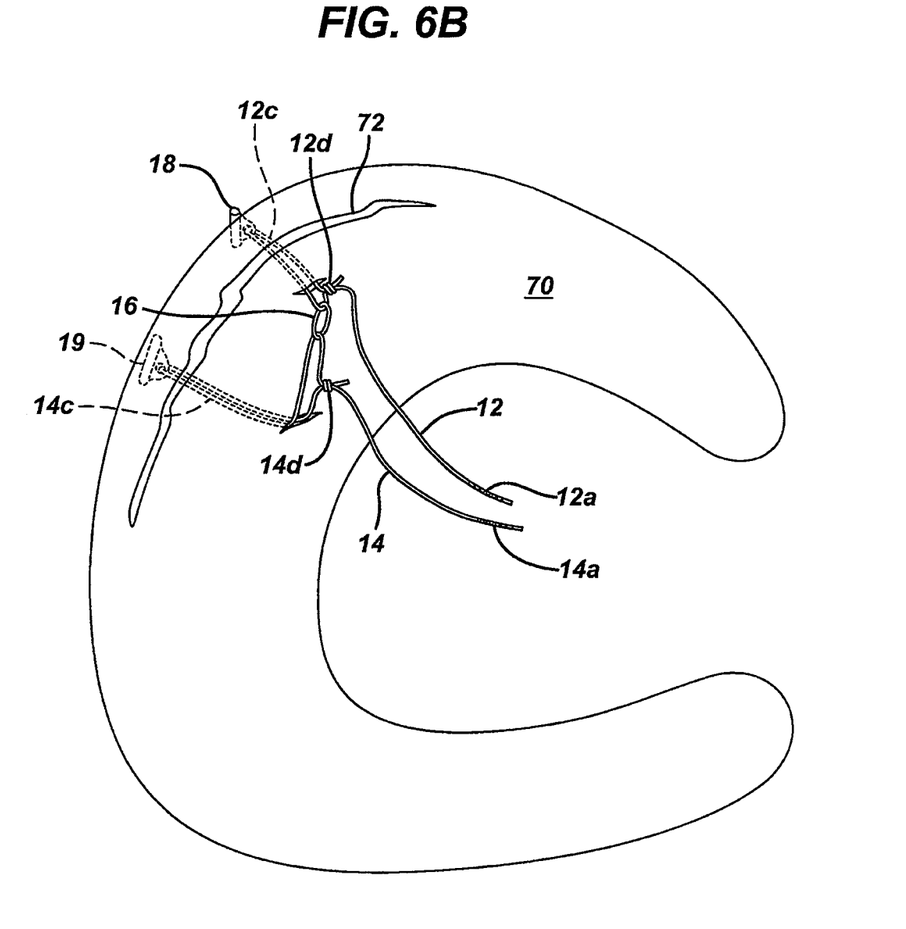
FIG. 6B is a perspective view illustration of a method for implanting a suture anchor system in accordance with the present invention, showing first and second suture anchors implanted through tissue to be repaired and into an anchoring tissue.
Figure 6C:
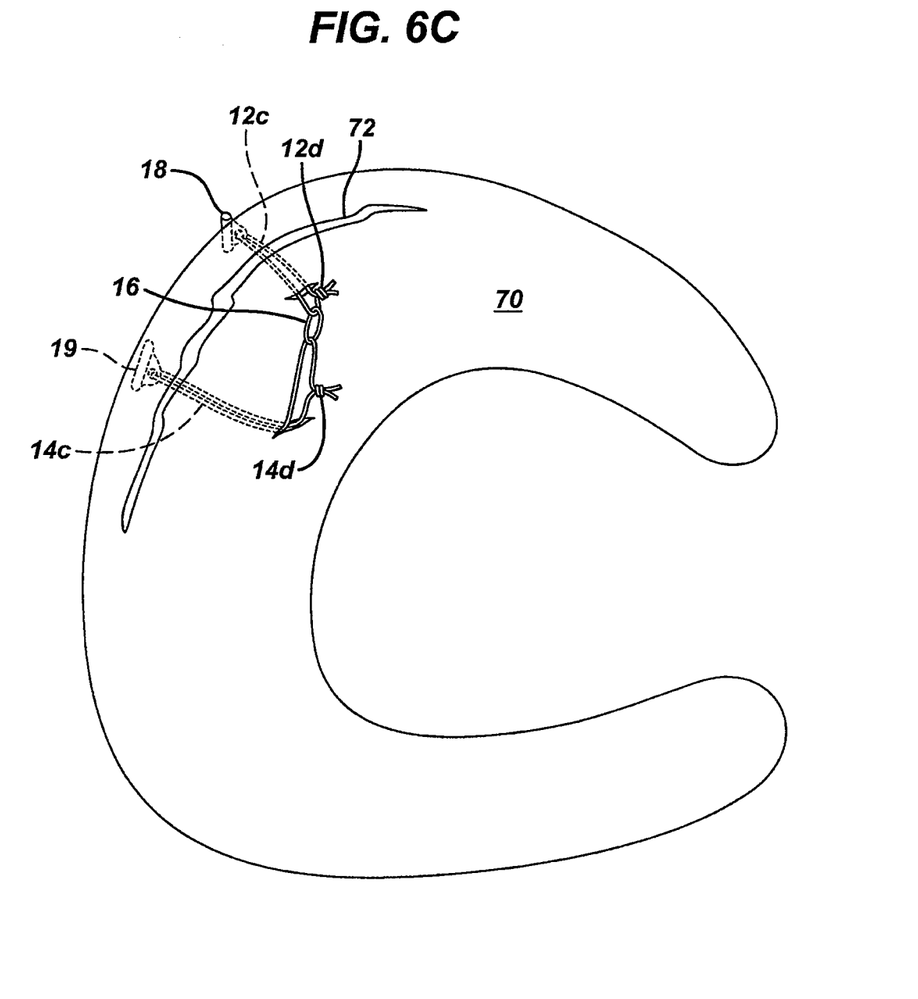
FIG. 6C is a perspective view illustration of a method for implanting a suture anchor system in accordance with the present invention, showing first and second suture anchors implanted through tissue to be repaired and into an anchoring tissue, and the suture length(s) tensioned to re-approximate and anchor the torn tissue to the anchoring tissue.

FIGS. 6A-6C illustrate an exemplary method for repairing torn or damaged tissue, in accordance with the present invention. While virtually any suture anchor system can be used to perform the method, FIGS. 6A-6C illustrate suture anchor system shown in FIG. 1 being used to repair torn tissue. In particular, FIGS. 6A-6C illustrate the meniscus of the knee being repaired, however a person skilled in the art will appreciate that the suture anchor systems and methods of the present invention can be used for a variety of medical procedures. One skilled in the art will also appreciate that the system of the invention is used with known and accepted arthroscopic surgical techniques, including patient preparation, anesthetization, and creation of one or more portals through a patient's skin.

At the outset, the suture anchors 18, 19 can be deployed into tissue using a variety of methods and devices. In the illustrated embodiment, however, the suture anchors 18, 19 are loaded onto a delivery device that is effective to deploy the anchor members through the tissue to be repaired and into the anchoring tissue, which can include bone and/or tissue. In general, the delivery device 60 is in the form of a generally elongate needle that is adapted to slidably receive each suture anchor 18, 19. The delivery device 60 also includes a trigger mechanism (not shown) that is effective to selectively advance each anchor member 18, 19 along the needle and through the tissue and/or bone.

A person skilled in the art will appreciate that a variety of other techniques can be used to deployed the members into the tissue to be repaired and into the anchoring tissue. Moreover, one skilled in the art will appreciate that the system of the invention is used with known and accepted arthroscopic surgical techniques, including patient preparation, anesthetization, and creation of one or more portals through a patient's skin.

Still referring to FIG. 6A, a meniscus of the knee 70 having to tear 72 formed therein is illustrated. The first suture anchor 18 is deployed through the meniscus 70 across the tear 72 and into anchoring tissue, which in the illustrated embodiment is a portion of the meniscus behind the tear. The anchoring tissue can also optionally include the joint capsule. The first suture loop 12c, which is attached to the first suture anchor 18, extends from the suture anchor 18 across the tear 72 and outward from the meniscus 70 to couple to the second suture loop 14c of the second suture length 14.

The second anchor 19 can then be deployed into the meniscus 70 across the tear 72 and into the anchoring tissue, as shown in FIG. 6B. Since the second suture loop 14c on the second anchor 19 is coupled to the third suture loop 16, which is coupled the first suture loop 12c on the first anchor 18, the suture loops 12c, 14c, 16c will extend from the first and second anchors 18, 19, through the tear 72, and across an external portion of the meniscus 70. The second anchor 19 should be deployed through the tissue at a position spaced apart from the first anchor member 18 by a selected distance. While the selected distance can vary depending on the tissue being repaired, the distance should be substantially equal to a diameter of the third suture loop 16c to allow the third suture loop 16c to extend across an external portion of the meniscus 70, and thereby engage the meniscus 70. This procedure can be repeated to implant additional suture anchors to facilitate repair of the tear.

Once the anchors 18, 19 are implanted, the terminal end 12a, 14a of each suture length 12, 14, which extends out from the meniscus 70, can be used to decrease the size of the first and second suture loops 12c, 14c, thereby pulling the third suture loop 16c taught against the external surface of the meniscus 70. This is achieved by pulling on or tensioning the terminal end 12a, 14a of each suture length 12, 14 to cause the slip knot 12d, 14d on each suture length 12, 14 to slide towards the anchor 18, 19. As a result, the torn tissue 72 is re-approximated toward the anchoring tissue to secure it to the anchoring tissue. The slip knot 12d, 14d on each suture length 12, 14 will prevent the suture loops 12c, 14c from expanding. Once the torn tissue 72 is repaired and anchored to the anchoring tissue, the terminal end 12b, 14b of each suture length 12, 14 can be trimmed, as shown in FIG. 6C.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture anchor system, comprising:
   a first suture anchor having an elongate body configured to engage tissue and a bore formed therein that slidably receives a first suture loop, the first suture loop including first and second terminal ends that are mated to one another to form a first knot;
   a second suture anchor having an elongate configured to engage tissue and a bore formed therein that slidably receives a second suture loop, the second suture loop including first and second terminal ends that are mated to one another to form a second knot that is separate from the first knot, and the second suture loop being slidably and directly coupled to the first suture loop and at least one of the first and second suture loops being selectively adjustable such that a distance between the first and second suture anchors with respect to each other is selectively adjustable.

2. The suture anchor system of claim 1, wherein the terminal ends of the first suture loop are fixedly mated to one another such that the first knot is a fixed knot, and the terminal ends of the second suture loop are adjustably mated to one another such that a size of the second suture loop is selectively adjustable and the second knot is an adjustable knot.

3. The suture anchor system of claim 2, wherein the second knot comprises a slip knot to enable selective adjustment of the size of the second suture loop.

4. The suture anchor system of claim 1, wherein the bore in the first and second suture anchors is oriented such that the first and second suture loops extend therethrough in a direction transverse to the elongate body.

5. The suture anchor system of claim 1, wherein the first knot comprises a slip knot configured to allow a size of the first suture loop to be adjusted, and the second suture loop has a fixed size.

6. A suture anchor system, comprising:
   a first suture loop passed through a bore formed in a first suture anchor, the first suture loop including a slip knot formed thereon to allow a size of the first suture loop to be adjusted; and
   a second suture loop slidably coupled to the first suture loop and passed through a bore formed in a second suture anchor, the second suture loop having a fixed size and including a second knot that is separate from the slip knot.

7. The suture anchor system of claim 6, wherein the first and second suture anchors each include a tissue-engaging portion and a suture-receiving portion having the bore formed therein.

* * * * *